(12) United States Patent
Gibson et al.

(10) Patent No.: US 12,023,011 B2
(45) Date of Patent: Jul. 2, 2024

(54) DEVICE FOR ACCESS TO THE INTERIOR OF A BODY

(71) Applicant: Joimax GmbH, Karlsruhe (DE)

(72) Inventors: Alastair Gibson, Edinburgh (GB);
Rainer Steegmüller, Magstadt (DE);
Wolfgang Ries,
Linkenheim-Hochstetten (DE)

(73) Assignee: JOIMAX GMBH, Karlsruhe (DE)

( * ) Notice: Subject to any disclaimer, the term of this patent is extended or adjusted under 35 U.S.C. 154(b) by 796 days.

(21) Appl. No.: 16/493,982

(22) PCT Filed: Mar. 6, 2018

(86) PCT No.: PCT/EP2018/000089
§ 371 (c)(1),
(2) Date: Sep. 13, 2019

(87) PCT Pub. No.: WO2018/166649
PCT Pub. Date: Sep. 20, 2018

(65) Prior Publication Data
US 2020/0121177 A1   Apr. 23, 2020

(30) Foreign Application Priority Data
Mar. 16, 2017 (DE) ..................... 10 2017 002 527.4

(51) Int. Cl.
*A61B 1/32* (2006.01)
*A61B 1/00* (2006.01)
*A61B 17/34* (2006.01)
*A61B 17/00* (2006.01)
*A61B 17/02* (2006.01)

(52) U.S. Cl.
CPC ............ *A61B 1/32* (2013.01); *A61B 1/00085* (2013.01); *A61B 17/3439* (2013.01); *A61B 2017/00867* (2013.01); *A61B 17/0218* (2013.01)

(58) Field of Classification Search
CPC ............ A61B 17/0218; A61B 17/3439; A61B 17/3421; A61B 1/32; A61B 1/00085; A61B 2017/3484
See application file for complete search history.

(56) References Cited

U.S. PATENT DOCUMENTS

| | | |
|---|---|---|
| 5,345,927 A | 9/1994 | Bonutti |
| 5,782,800 A | 7/1998 | Yoon |
| 5,817,062 A | 10/1998 | Flom et al. |
| 8,636,778 B2 * | 1/2014 | Gephart ............. A61B 17/7037 606/267 |
| 10,390,694 B2 * | 8/2019 | Farin .................. A61B 17/0485 |

(Continued)

FOREIGN PATENT DOCUMENTS

| | | |
|---|---|---|
| CN | 1897868 A | 1/2007 |
| CN | 102526862 A | 7/2012 |

(Continued)

*Primary Examiner* — Jan Christopher L Merene
(74) *Attorney, Agent, or Firm* — McGlew and Tuttle, P.C.

(57) ABSTRACT

A device is configured to provide a large visible area and work area in the body of a patient for access to the interior of a body. The device has at least one outer part having an outer tube. An inner tube passes into the outer tube through this outer tube having at an outer tube distal end an expanding part which is expandable beyond the outer diameter of the outer tube.

21 Claims, 5 Drawing Sheets

(56) References Cited

U.S. PATENT DOCUMENTS

| | | | |
|---|---|---|---|
| 2003/0216770 A1* | 11/2003 | Persidsky | A61B 17/3439 606/198 |
| 2003/0220644 A1 | 11/2003 | Thelen et al. | |
| 2005/0267331 A1 | 12/2005 | Secrest et al. | |
| 2006/0041270 A1 | 2/2006 | Lenker et al. | |
| 2007/0149845 A1* | 6/2007 | Kuhns | A61B 1/00087 600/101 |
| 2008/0058591 A1 | 3/2008 | Saadat et al. | |
| 2008/0306442 A1* | 12/2008 | Bardsley | A61B 17/3439 604/164.04 |
| 2010/0240959 A1 | 9/2010 | Donahue | |
| 2013/0197592 A1 | 8/2013 | Mafi | |
| 2013/0345739 A1* | 12/2013 | Brady | A61B 17/320725 606/200 |
| 2014/0025045 A1 | 1/2014 | Abt et al. | |
| 2014/0046435 A1 | 2/2014 | Yeung et al. | |
| 2014/0378985 A1 | 12/2014 | Mafi | |

FOREIGN PATENT DOCUMENTS

| | | |
|---|---|---|
| CN | 103118605 A | 5/2013 |
| DE | 102013004964 A1 | 9/2014 |
| JP | 2004-237099 A | 8/2004 |
| JP | 2010526157 A | 7/2010 |
| JP | 2010-527265 A | 8/2010 |
| JP | 2013183933 A | 9/2013 |

* cited by examiner

DEVICE FOR ACCESS TO THE INTERIOR OF A BODY

CROSS REFERENCE TO RELATED APPLICATIONS

This application is a United States National Phase Application of International Application PCT/EP2018/000089, filed Mar. 6, 2018, and claims the benefit of priority under 35 U.S.C. § 119 of German Application 10 2017 002 527.4, filed Mar. 16, 2017, the entire contents of which are incorporated herein by reference.

TECHNICAL FIELD

The present invention pertains to a device for access to the interior of a body, having at least one outer part having an outer tube.

TECHNICAL BACKGROUND

Such (outer) tubes or sleeves are inserted from the surface of a human body or animal body into the interior by means of known techniques, such as especially via dilators creating and expanding an insertion duct, as this is described, for example, in DE 10 2013 004 964 A1, among others. Through the tube or the sleeve thus placed, an endoscope can then be inserted or working instruments can be inserted in order to perform surgical procedures in the distal end area of the tube or beyond same, for example, to remove in an intervertebral space parts of a disk pinching a nerve of the spine, to insert into vertebrae material for stabilizing same or the like.

A drawback is that the visible area and work area at the distal end of the tube is defined by the tube diameter itself. In particular, the tube diameter has to be a compromise, since one would like to not pass through the skin of a patient at the passage location with a very large diameter of tubes in order to minimize lesions as much as possible and to reduce scar formation.

US 2013/0197592 A1 discloses an anchoring cannula with a tube, the end of which is provided with a spreading part which has strips running distally from the distal end and which are interconnected by a "shape-set" material. Within an outer tube, the strips are held by this in parallel and paraxial alignment, while they conically set up on exiting the outer tube. The expansion part is preferably made of a polymer

SUMMARY

An object of the present invention is to keep the impacts as minimal as possible while maintaining the last-mentioned conditions, namely especially in the skin area, and yet to provide a field of view and work area that are as optimal and as large as possible.

This object is accomplished according to the present invention with a device of the type mentioned in the introduction, which is characterized in that an inner tube passing into the outer tube through this outer tube has at its distal end an expanding part that is expandable beyond the outer diameter of the outer tube.

Due to the expanding part of the inner tube, which expanding part expands when released from the outer tube beyond the diameter thereof, surrounding (soft) tissue is pressed to the side and a visible area and work area with a greater diameter is thus provided than this is or was the case up to now. The work of the surgeon is thus made easier and is less stressful and also safer for the patient.

Provisions are made in a preferred variant for the expanding part to be configured as a grid, wherein especially the expanding part is configured as a grid with diamond-shaped openings. Due to this structural configuration of the expanding part, biocompatible materials, such as especially Nitinol for at least the expanding part or else also stainless steel can be inserted and other more problematic materials, as they would be present, for example, in case of an umbrella-like expansion or openings of the expanding part in case of other materials, can be avoided.

A preferred variant makes provisions here for the diameter of the expanding part in the expanded configuration thereof to extend conically expanding in the distal direction from a transition area towards the inner tube. The expanding part in its expanded configuration is adapted in such a way to the other working elements and the surrounding area by its distal end having the greatest width, while the proximal transition of the expanding part towards the distal end of the inner tube and outer tube is rather continuous.

Another extremely preferred embodiment provides for the expanding part to have a cylindrical configuration in its distal area in an expanded configuration. The risk of injury is thus reduced.

Provisions are made here in a concrete embodiment for the expanding part to be formed by struts, which are connected to one another, and by slots which are located between these struts, wherein especially one strut is connected via a connection point to struts extending directly adjacent to this one strut in the circumferential direction.

Variants of the device according to the present invention provide for two struts arranged next to one another in the circumferential direction to be connected via a connection point to struts which are axially directly adjacent to them, and especially four struts enclose a diamond-shaped intermediate space when the expanding part is expanded.

Provisions may be made in this connection for struts following one another and enclosing a diamond-shaped intermediate space in the expanded configuration to have different lengths, wherein especially struts of different lengths following one another are formed in the proximal area of the expanding part. In other areas of the expanding part, provisions may be made for struts axially following one another and defining a diamond-shaped intermediate space in the expanded configuration to have equal lengths, wherein especially struts following one another have equal lengths in the distal area of the expanding part.

The risk of injury of surrounding tissue is, furthermore, reduced by provisions preferably being made for free distal ends of the struts to be rounded off.

The material of at least the expanding part of the inner tube and of the inner part is extremely preferably made of Nitinol, even though it may also be made, in principle, of other biocompatible materials, for example, stainless steel. In this case, Nitinol has the advantage that it has two temperature-dependent stable states. Thus, the expanding part in a low-temperature configuration may have at low temperatures a compressed, continuous cylindrical configuration for inserting in and through the outer tube (outside of the body of a patient) and during insertion with the outer tube into the body of the patient, while the expanding part is then only expanded when moving out of the distal end of the outer tube and expands to its essentially expanded configuration, in which, as said, the extremely distal area preferably has, in turn, a cylindrical configuration.

In order to provide a secure connection of the expanding part to an inner tube which is usually made of stainless steel, since the two materials can be connected in substance only poorly, especially can be welded only to a limited extent, provisions are first made for the expanding part to be configured in one piece with a distal tube section of the inner tube, which distal tube section is likewise made of Nitinol, wherein, moreover, provisions are then made for the distal tube section and proximal tube section of the inner tube to be connected to one another in a positive-locking manner. To carry out the positive-locking connection, provision is made, in particular, for the distal tube section to have in its proximal area slots which protrude up to its proximal end face and which extend especially from recesses which bypass the radial projections of the proximal tube section.

Another preferred embodiment provides for the outer tube and the inner tube to have grip parts, which interact with one another at their proximal ends and which form a common grip in case of an expanded configuration of the expanding part, wherein especially a distal section of the grip part of the inner part has an external thread, which interacts with a pin of the grip part of the outer tube, which pin protrudes inwards and meshes with this external thread. As a result, the expanding part of the outer tube can be led out in a defined, controlled and targeted manner, wherein this outer tube is preferably moved back with certainty by the inner part and the outer part being rotated in relation to one another and an axial movement of the two parts in relation to one another thus being brought about due to the screw-like connection.

For connecting the outer tube and/or the inner tube to the respective grip part, provisions are made in another preferred embodiment for the outer tube to be connected in a positive-locking manner to a first grip part of a grip and/or for the inner tube to be connected in a positive-locking manner to a second grip part of a grip, wherein especially the outer tube and/or the inner tube has/have each at their proximal end lugs directed outwards with undercuts that include lug undercut edges that extend behind undercut edges of undercuts formed on the inner side of the respective grip part.

Additional advantages and features of the present invention appear from the claims and from the following description, in which an exemplary embodiment of the present invention is explained with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 3A:
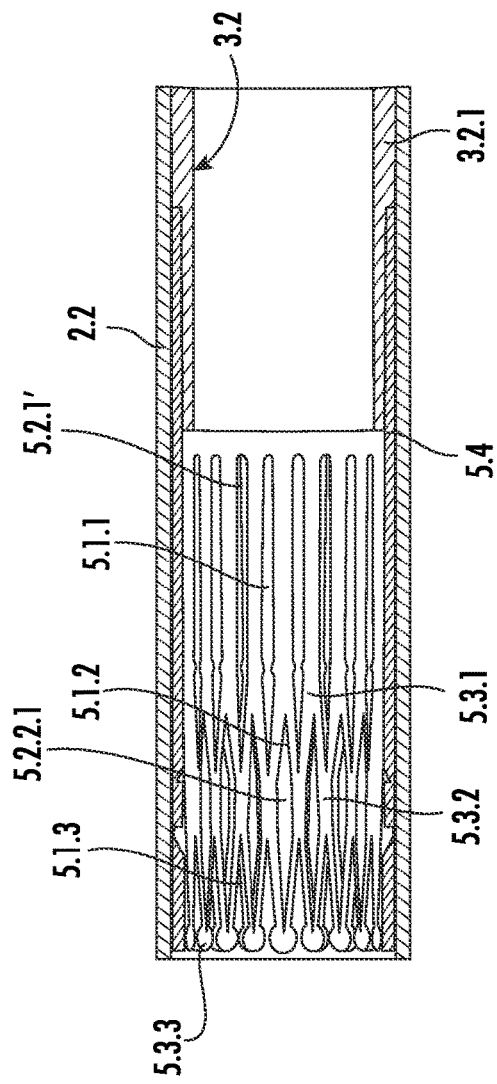
FIG. 3*a* is an enlarged sectional view of the distal end according to FIG. 3.
Figure 3:
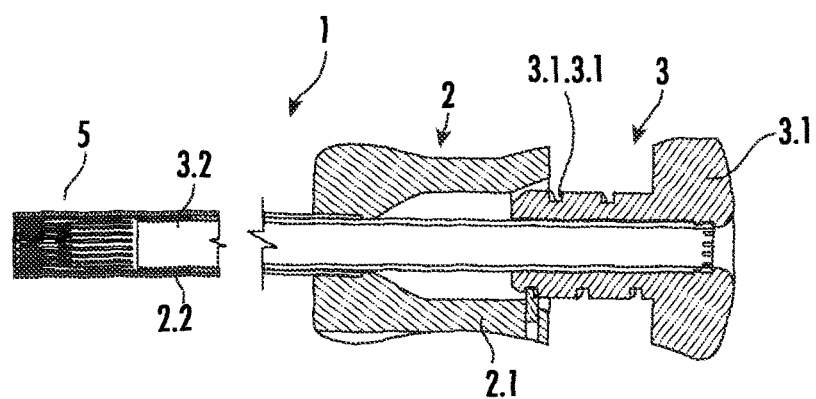
FIG. 3 is a longitudinal sectional view through a device according to the present invention in an insertion configuration of same.
Figure 5:
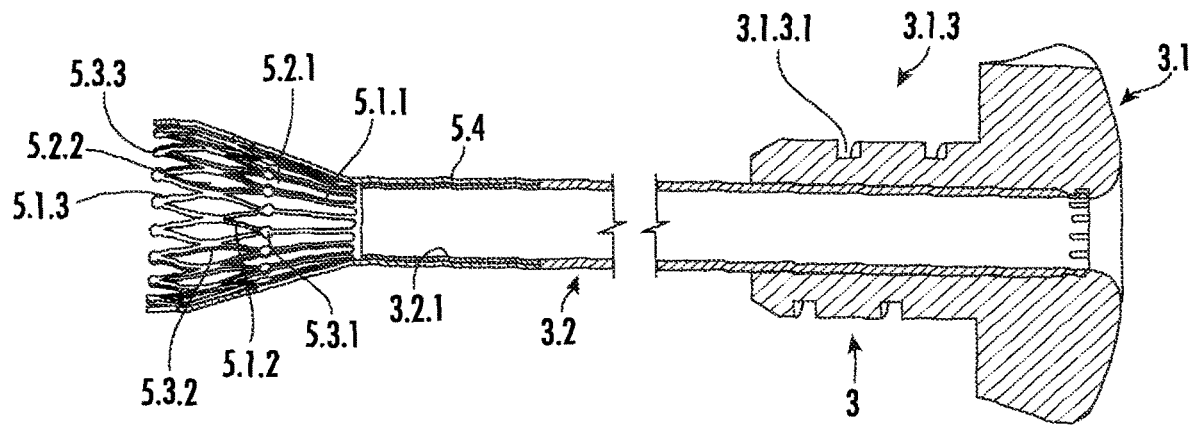
FIG. 5 is a longitudinal sectional view through the inner part of the device according to the present invention in a view somewhat enlarged compared to FIG. 4.

Referring to the drawings, the device 1 according to the present invention for access to a body has an outer part 2 and an inner part 3 (especially FIGS. 3, 5).

Figure 1:
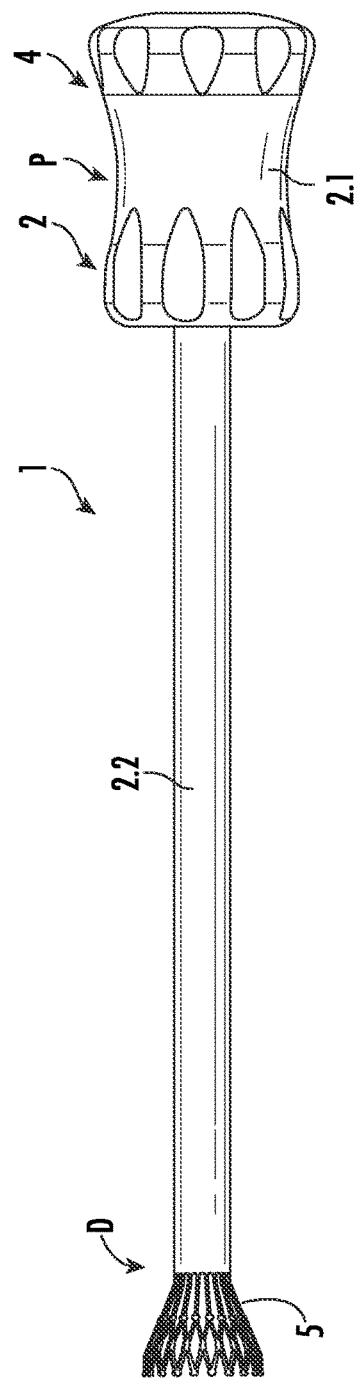
FIG. 1 is a lateral view showing a device according to the present invention in working configuration.
Figure 2:
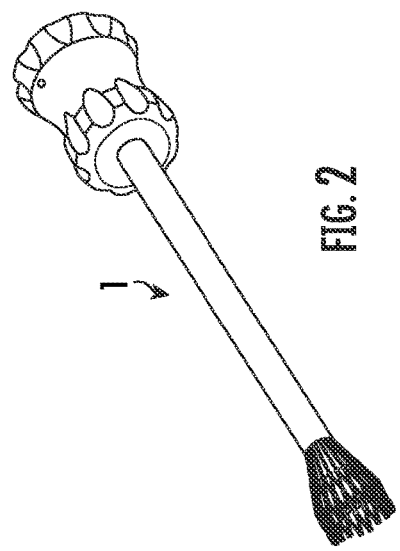
FIG. 2 is a perspective view showing the device from FIG. 1 with an oblique view of the expanded distal end.

The outer part 2 has a proximal end area P of the device, a first grip part 2.1 and, moreover, an outer tube 2.2. The inner part 3 has first a second grip part 3.1 and, moreover, an inner tube 3.2 that can be inserted into the outer tube 2.2 and can be passed through this outer tube 2.2. The first grip part 2.1 and the second grip part 3.1 together form a single grip 4, for example, in the working configuration shown in FIGS. 1 and 2.

The inner part 3 has at its distal end D an expanding part 5. This expanding part 5 is made of Nitinol and has an expanded expanding configuration at least at a transition temperature of at least 25° C., preferably 28° C., above the ambient temperature of approx. 20° C. to 22° C., as it can be seen for the expanding part in all the figures showing same, except for FIG. 3*a*.

The expanding part 5 preferably has an independent contracted configuration at lower temperatures below the transition temperature, as they correspond to the view according to FIGS. 3, 3*a* within the outer tube. The expanding part made of Nitinol is the preferred embodiment. As an alternative, provisions may also be made for the expanding part 5 to be made of the same material or of a different material, such as stainless steel, with a stable expanding configuration corresponding, for example, to FIG. 4 due to an insertion element extending conically inwards being forcibly radially compressed from the distal end of the outer part 2 or of the outer tube 2.2 thereof and in this manner being inserted into the outer tube 2.2.

The expanding part 5 is configured as a grid in the form of a tulip. It has individual struts 5.1.1, 5.1.2, 5.1.3, between which are formed in the compressed or low-temperature configuration (FIG. 3*a*) slots 5.2.1', 5.2.2', which expand towards intermediate spaces between the struts 5.1.1, 5.1.2 in the form of diamonds 5.2.1, 5.2.2 (for example, FIG. 5) in the expanded or high-temperature configuration. The diamonds 5.2.1, 5.2.2 may have a symmetrical (5.2.2) or asymmetrical (5.2.1) configuration here, namely in relation to a radial plane of the expanding part due to their respective areas of greater width in the longitudinal direction. The struts 5.1.2, 5.1.3 enclosing an intermediate space in the form of a diamond 5.2.1, 5.2.2 have the same length or else two struts 5.1.1, 5.1.2 have respectively different lengths; the struts 5.1.1 are thus longer than the struts 5.1.2, 5.1.3 of the same diamonds.

Figure 6:
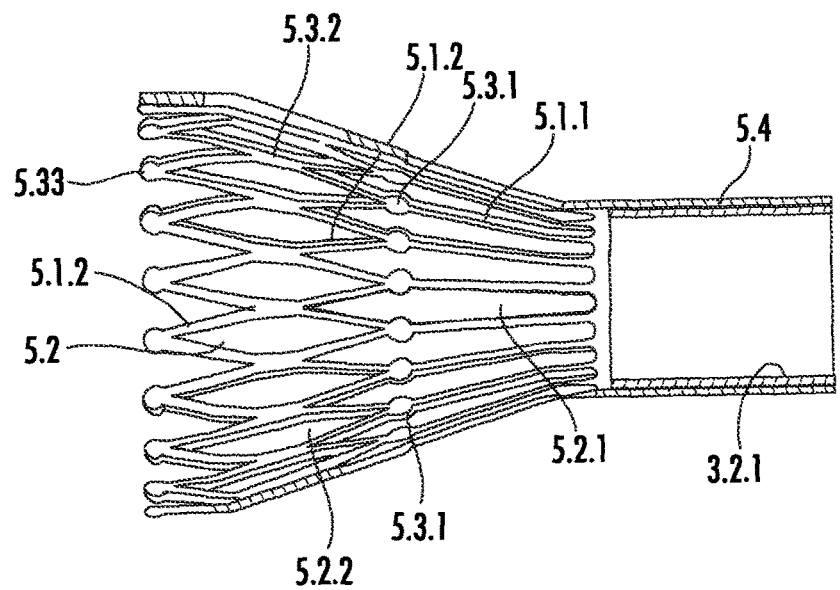
FIG. 6 is a longitudinal sectional view through the distal end of the inner part of the device according to the present invention.

One strut 5.1.1, 5.1.2, 5.1.3 is an elongated metal section of the expanding part 5 from a connection point 5.3.1 with another strut up to another connection point with a third strut (especially FIG. 6). It appears especially from FIG. 6 that the proximal struts 5.1.1 forming the intermediate space diamond 5.2.1 there have a longer configuration than the struts 5.1.2 forming the same diamond 5.2.1 distally following the struts 5.1.1, while the intermediate space diamond 5.2.2 distally following the diamond 5.2.1 is formed by struts 5.1.2, 5.1.3 of equal length enclosing it. The proximal connection point 5.3.1 connects three struts, namely a strut 5.1.1 with two struts 5.1.2. The middle connection point 5.3.2 connects four struts 5.1.2, 5.1.3 of equal length and the connection point formed at the distal end of the expanding part 5 connects two struts 5.1.3.

The expanding part 5 is configured in one piece with a distal tube section 5.4 of the inner tube 3.2. The tube section 5.4 is configured in one piece with the expanding part 5 and is likewise preferably made of Nitinol, while the tube section 3.2.1 configured in one piece with the inner tube 3.2 as well as this inner tube 3.2 are made of stainless steel. The tube section 5.4 overlaps a distal end section 3.2.1, wherein the section 5.4 encloses the section 3.2.1 on the radially outer side. The tube section 5.4 and the tube section 3.2.1 are connected to one another in a positive-locking manner, providing a physical barrier against disconnection, as this is shown in FIGS. 7 and 8, since connections in substance can be made only poorly; in particular, a welded connection between the materials Nitinol and stainless steel is not possible and adhesive compounds made of organic substances are not allowable in case of elements inserted into a human body and, in addition, are not reliable, since a separation is not ruled out here.

Figure 7:
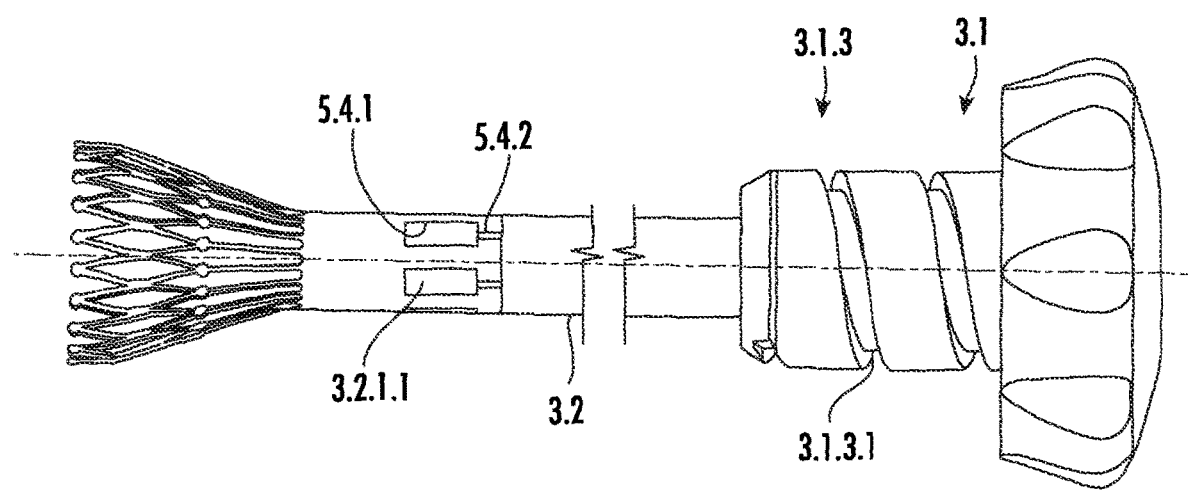
FIG. 7 is a lateral view of the inner part of the device according to the present invention corresponding to FIG. 5.
Figure 8:
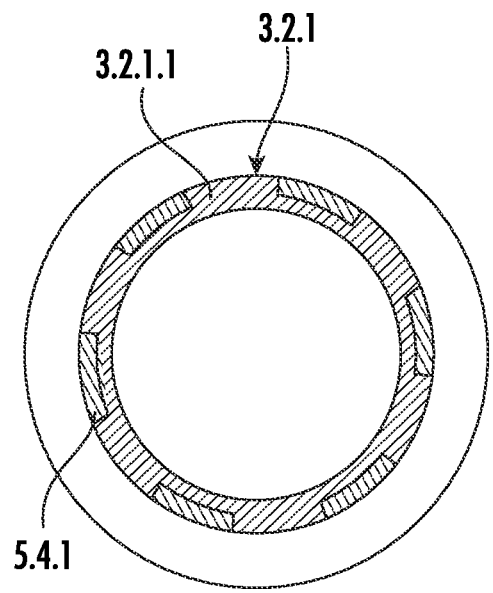
FIG. 8 is a longitudinal view of the inner tube of the device according to the present invention corresponding to E-E according to FIG. 7.

The positive-locking connection is configured such that the tube section 3.2.1 of the inner tube 3.2 has rectangular projections 3.2.1.1 configured in one piece on its outer side, while the tube section 5.4 has rectangular recesses 5.4.1 adapted to this inner tube 3.2 and overlaps the projections 3.2.1.1 with this tube section 5.4, as this can be seen especially in FIG. 7. So that the tube section 5.4 can be pushed over the tube section 3.2.1, slots 5.4.2 are formed at the tube section 5.4 proximally to the recesses 5.4.1 (FIG. 7).

Consequently, a reliable positive-locking connection of the two tube sections 5.4 and 3.2.1 can be achieved. The formation of the projections 3.2.1.1, on the one hand, and of the recesses 5.4.1, on the other hand, preferably takes place by machining, for example, by laser cutting, milling, grinding or even with regard to the projections 3.2.1.1 by etching away of areas of the tube section 3.2.1 in areas enclosing the projections 3.2.1.1.

Figure 9:
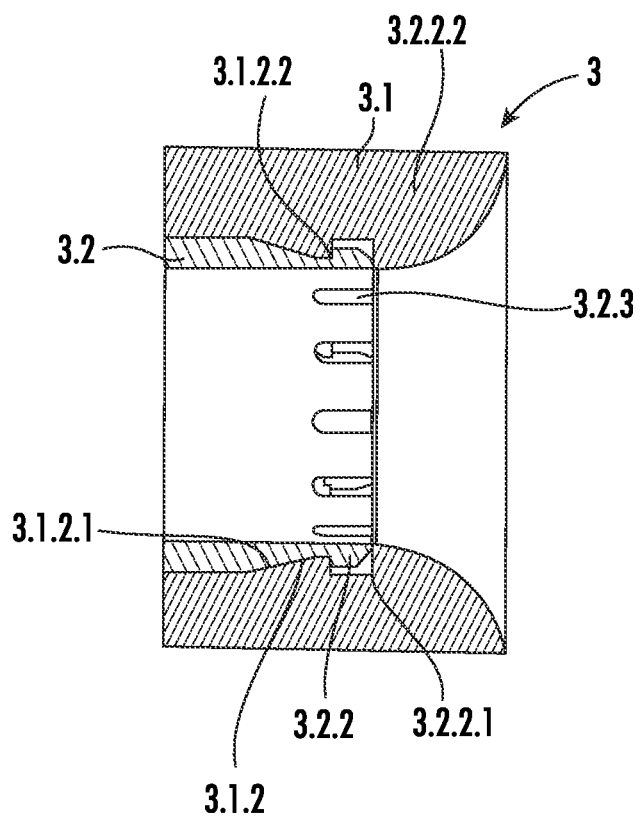
FIG. 9 is an enlarged, longitudinal section, detail view of the proximal area of the inner part of the device according to the present invention.

The inner tube 3.2 is likewise connected in a positive-locking manner to the grip part 3.1 at its proximal end, as this is shown in FIG. 9.

For this, the inner tube 3.2 has at its proximal end lugs 3.2.2 extending radially, which are formed by a tapering of the wall of the inner tube 3.2, which tapering is provided directly distally to the lugs 3.2.2. The tapering may likewise again be provided by machining or by etching in the manner described. So that the lugs 3.2.2 can yield in the radially inwards direction, slots 3.2.3 are formed between them. The lugs extend behind a projection 3.1.2 of the grip part 3.1, which projection 3.1.2 extends protruding inwards. So that they can slide by this projection 3.1.2 from the distal direction into respective recesses/undercuts to establish the positive-locking connection, this projection 3.1.2 has on its distal side 3.1.2.1 a bevel as well as the projections 3.1.2 at their proximal end 3.2.2.1, while the proximal end face 3.1.2.2 of the lug 3.2.2 and the distal side 3.2.2.2 of the lug 3.2.2 are each directed in the radial direction.

Consequently, a secure and reliable positive-locking connection of the inner tube 3.2 and the grip part 3.1 of the inner part 3 can be provided.

Figure 10:
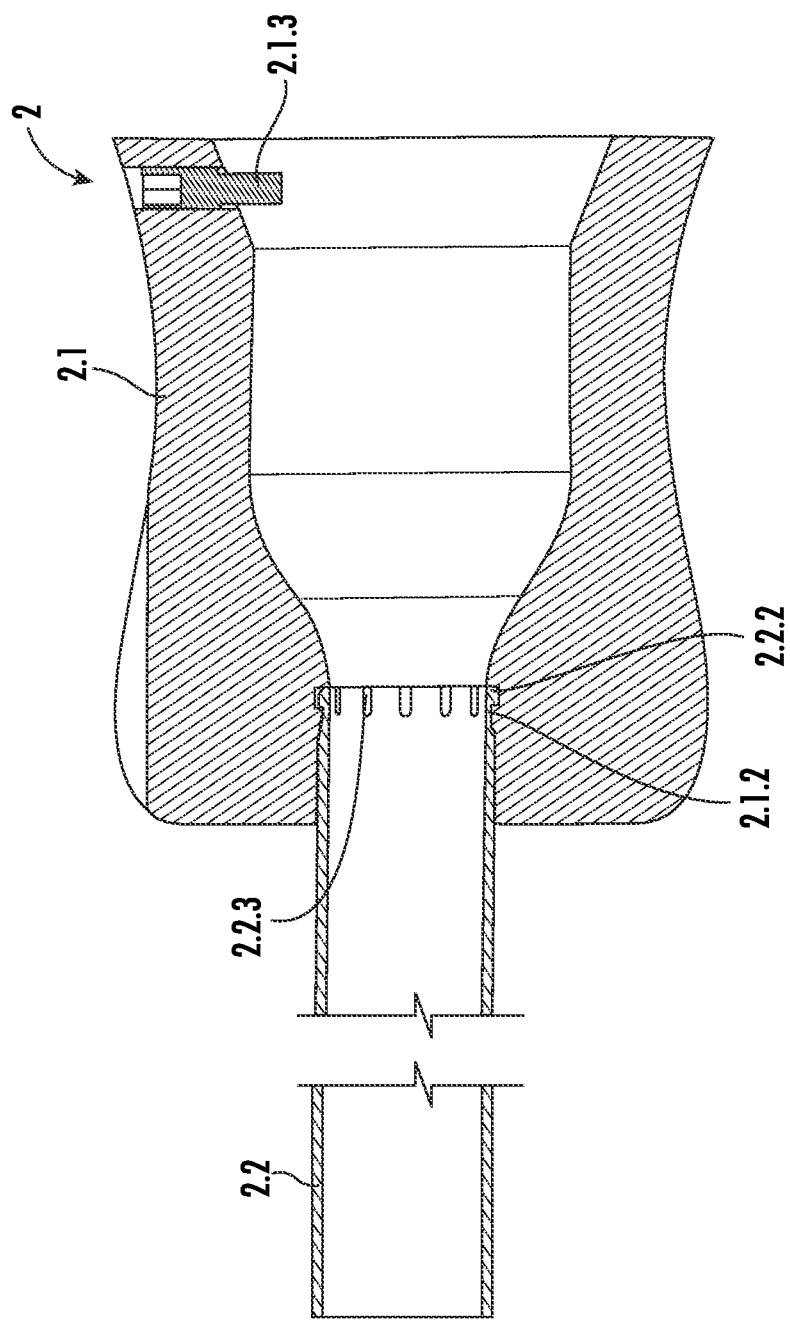
FIG. 10 is a longitudinal sectional view corresponding to FIG. 9 of the proximal area of the outer part of the device according to the present invention.

FIG. 10 shows that the outer tube 2.2 is connected in a positive-locking manner to its grip part 2.1 in the same manner.

For this, the outer tube 2.2, just like the inner tube 3.2, has at its proximal end lugs 3.2.2 extending radially, which are formed by tapering of the wall of the inner tube 3.2 directly distally to the lugs 2.2.2. The tapering may likewise be formed by machining or by etching. So that the lugs 2.2.2 can yield in the radially inward direction, slots 2.2.3 are formed between them. The lugs 2.2.2 extend behind a projection 2.1.2 of the grip part 2.1, which projection 2.1.2 extends protruding inwards. So that they can slide by this projection 2.1.2 from the distal direction to establish the positive-locking connection, this projection 2.1.2 has a bevel on its distal side, just like the lugs 2.2.2 at their proximal end, while the proximal end face of the lug 2.2.2 and the distal side of the lug 2.2.2 are each directed in the radial direction.

Consequently, a secure and reliable positive-locking connection of the outer tube 2.2 and the grip part 2.1 of the outer part 2 can be provided.

The outer part 2 and the inner part 3 are connected to one another movable in relation to one another in the following manner: due to a rotary movement of the parts in relation to one another, an axial movement of same in relation to one another also takes place. For this, the grip part 3.1 of the inner part 3 (especially FIGS. 5, 7) has over a distal section 3.1.3 an external screw thread 3.1.3.1, with which a pin 2.1.3 protruding inwards meshes at the proximal end of the grip part 2.1 of the outer part 2, as this can be found in the comparison of FIGS. 3 and 4 in addition to in FIGS. 5, 7, 10.

Figure 4:
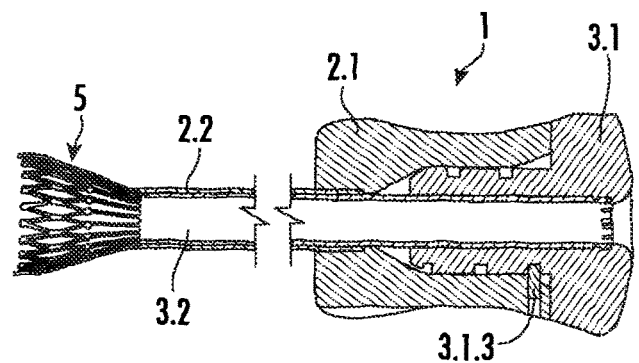
FIG. 4 is a longitudinal sectional view corresponding to FIG. 2 of the device in working configuration corresponding to FIG. 1.

The device 1 according to the present invention is used as follows:

When the expanding part 5 is made of Nitinol, the inner tube 3.2 of the inner part 3 is first inserted into the outer tube 2.2 of the outer part 2 up to the position shown in FIG. 3 at a relatively low temperature by the expanding part 5 occupying its compressed position shown in FIG. 3, i.e., without the expanding part 5 protruding from the distal end of the outer tube 2.2. In this case, the pin 2.1.3 meshes with this outer tube 2.2 at the distal end of the screw thread 3.1.3.1. The device is then inserted in this configuration up to the work site in the interior of a body, such as of a human or animal body. The inner part and the outer part are then rotated in relation to one another, as a result of which the expanding part 5 is moved out of the distal end of the outer tube 2.2, as this is shown in FIG. 4, until it assumes its expanded or high-temperature configuration shown there.

The length of the expanding part is preferably 8 mm to 28 mm, especially 18 mm, while the diameter is in the range of 5 mm to 30 mm, especially at 17 mm to 18 mm. The ratio of the length to the diameter of the expanding part 5 is especially between 0.25 and 1, preferably at 0.7 to 0.8. In addition, the diameter of the distal end of the expanding part 5 in the expanded or high-temperature position is 1.5 times or 2.5 times, preferably 2 times, the diameter of the tubes 2.2, 2.3.

The function of the expanding part 5 is to push body tissue surrounding same aside and thus to achieve a radially larger free area for viewing through an endoscope, on the one hand, and to expand, for example, soft tissue in front of bone parts, such as vertebrae of the spine with regard to working by means of instruments, on the other hand, so that a larger field of vision on the vertebrae or an intervertebral space is provided and a larger field of vision and work area on or at a vertebrae or on or at an intervertebral space is provided. Consequently, the work of a surgeon is made substantially easier.

While specific embodiments of the invention have been shown and described in detail to illustrate the application of the principles of the invention, it will be understood that the invention may be embodied otherwise without departing from such principles.

The invention claimed is:

1. A device for access to the interior of a body, the device comprising:
    at least one outer part comprising an outer tube;
    an inner tube passing into the outer tube through the outer tube, the inner tube having an inner tube distal tube section with an outer side having radial projections at a distal end of the inner tube distal tube section; and
    an expansion part comprising a proximal section and an expansion section configured to be self-expanding from a compressed configuration to an expanded configuration, wherein the expansion section is in the compressed configuration within a diameter of the outer tube and the expansion section is in the expanded configuration outside the diameter of the outer tube, which is expanded beyond the diameter of the outer tube, with the expansion section extended out of a distal end of the outer tube, the proximal section of the expansion part being connected to the inner tube at the inner tube distal tube section with a positive-locking connection with respect to an axial disconnection direction, wherein the radial projections of the inner tube distal tube section mesh with radially recesses in the proximal section of the expansion part to form the positive-locking connection,
    wherein the outer tube is positive-lockingly connected to a first grip part of a grip, and/or the inner tube is positive-lockingly connected to a second grip part of the grip; and
    wherein the first grip part of the grip has an inner side with a first grip part undercut having a first grip part undercut edge and the outer tube has an outwardly directed first part lug at an outer tube proximal end, the first part lug being configured to extend behind the first grip part undercut edge; and/or the second grip part of the grip has an inner side with a second grip part undercut having a second grip part undercut edge and the inner tube has an outwardly directed second part lug at an inner tube proximal end, the second part lug being configured to extend behind the second grip part undercut edge.

2. A device in accordance with claim 1, wherein the recesses in the proximal section of the expansion part encompass and/or surround the radial protections of the proximal section of the inner tube.

3. A device in accordance with claim 1, wherein the proximal section of the expansion part is configured as a proximal tube section.

4. A device in accordance with claim 1, wherein the expansion part is made of Nitinol.

5. A device in accordance with claim 1, wherein the inner tube distal tube section is made of stainless steel.

6. A device in accordance with claim 3, wherein the expansion section of the expansion part is made of Nitinol and is configured in one piece with the proximal tube section which is likewise made of Nitinol.

7. A device in accordance with claim 1, wherein the expansion section of the expansion part is configured as a grid.

8. A device in accordance with claim 1, wherein in the expanded configuration, the expansion section of the expansion part is configured as a grid with diamond-shaped openings.

9. A device in accordance with claim 1, wherein a diameter of the expansion section of the expansion part in the expanded configuration thereof extends conically, expanding in the distal direction from a transition area towards the inner tube.

10. A device in accordance with claim 1, wherein with the expansion section of the expansion part in the expanded configuration a distal area of the expansion section has a cylindrical configuration.

11. A device in accordance with claim 1, wherein the expansion section of the expansion part is formed by struts, which are connected to one another, and by slots which are located between the struts, wherein one strut is connected via a connection point to adjacent struts extending directly adjacent to said one strut, in the circumferential direction.

12. A device in accordance with claim 1, wherein:
    the expansion section of the expansion part is formed by struts, which are connected to one another, and by slots which are located between the struts; and
    two struts arranged next to one another in the circumferential direction are connected via a connection point to struts which are axially directly adjacent to said two struts.

13. A device in accordance with claim 1, wherein:
    the expansion section of the expansion part is formed by struts, which are connected to one another, and by slots which are located between the struts; and
    four struts enclose a diamond-shaped intermediate space when the expansion section of the expansion part is expanded to the expanded configuration.

14. A device in accordance with claim 1, wherein:
    the expansion section of the expansion part is formed by struts, which are connected to one another, and by slots which are located between the struts; and
    struts following one another and enclosing a diamond-shaped intermediate space in the expanded configuration have different lengths, wherein struts of different lengths following one another are formed in the proximal area of the expansion section of the expansion part.

15. A device in accordance with claim 1, wherein:
    the expansion section of the expansion part is formed by struts, which are connected to one another, and by slots which are located between the struts; and
    struts axially following one another and defining a diamond-shaped intermediate space in the expanded configuration have equal lengths, wherein struts following one another have equal lengths in the distal area of the expansion section of the expansion part.

16. A device in accordance with claim 1, wherein:
    the expansion section of the expansion part is formed by struts, which are connected to one another, and by slots which are located between the struts; and
    free distal ends of the struts are rounded off.

17. A device in accordance with claim 1, wherein:
    the outer tube has the first grip part as an outer tube grip part with a pin;

the inner tube has the second grip part as an inner tube grip part;

the outer tube grip part and the inner tube grip part interact with one another at an outer tube proximal end and at an inner tube proximal end to form a common grip in the expanded configuration of the expansion section of the expansion part;

a distal section of the inner tube grip part has an external thread, which interacts with the pin of the outer tube grip part, the pin protrudes inwards and meshes with the external thread.

18. A device according to claim 2, wherein the proximal section of the expansion part has slots which extend from the recesses of the expansion part up to a proximal end face of the expansion part.

19. A device for access to the interior of a body, the device comprising:
   at least one outer part comprising an outer tube;
   an inner tube passing into the outer tube through the outer tube, the inner tube having an inner tube distal tube section with an outer side having radial projections at a distal end of the inner tube distal tube section, wherein the inner tube distal tube section is made of stainless steel; and
   an expansion part comprising a proximal section and an expansion section configured to be self-expanding from a compressed configuration to an expanded configuration, wherein the expansion section is in the compressed configuration within a diameter of the outer tube and the expansion section is in the expanded configuration outside the diameter of the outer tube, which is expanded beyond the diameter of the outer tube, with the expansion section extended out of a distal end of the outer tube, the proximal section of the expansion part being connected to the inner tube at the inner tube distal tube section with a positive-locking connection with respect to an axial disconnection direction, wherein the radial projections of the inner tube distal tube section mesh with radially recesses in the proximal section of the expansion part to form the positive-locking connection, wherein the expansion section of the expansion part is made of Nitinol and is configured in one piece with the proximal tube section which is likewise made of Nitinol,
   wherein the outer tube is positive-lockingly connected to a first grip part of a grip, and/or the inner tube is positive-lockingly connected to a second grip part of the grip; and
   wherein the first grip part of the grip has an inner side with a first grip part undercut having a first grip part undercut edge and the outer tube has an outwardly directed first part lug at an outer tube proximal end, the first part lug being configured to extend behind the first grip part undercut edge; and/or the second grip part of the grip has an inner side with a second grip part undercut having a second grip part undercut edge and the inner tube has an outwardly directed second part lug at an inner tube proximal end the second part lug being configured to extend behind the second grip part undercut edge.

20. A device for access to the interior of a body, the device comprising:
   at least one outer part comprising an outer tube;
   an inner tube passing into the outer tube through the outer tube, the inner tube having an inner tube distal tube section with an outer side having radial projections at a distal end of the inner tube distal tube section; and
   an expansion part comprising a proximal section and an expansion section configured to be self-expanding from a compressed configuration to an expanded configuration, wherein the expansion section is in the compressed configuration within a diameter of the outer tube and the expansion section is in the expanded configuration outside the diameter of the outer tube, which is expanded beyond the diameter of the outer tube, with the expansion section extended out of a distal end of the outer tube, the proximal section of the expansion part being connected to the inner tube at the inner tube distal tube section with a positive-locking connection with respect to an axial disconnection direction, wherein the radial projections of the inner tube distal tube section mesh with radially recesses in the proximal section of the expansion part to form the positive-locking connection,
   wherein the outer tube is positive-lockingly connected to a first grip part of a grip, and/or the inner tube is positive-lockingly connected to a second grip part of the grip; and
   wherein that the outer tube and/or inner tube have at their proximal end outwardly directed lugs with lug undercuts having lug undercut edges which engage behind grip undercut edges of grip undercuts formed on the inside of the grip, the lug undercuts being formed by a tapering of the wall of the outer tube and/or inner tube, which tapering is provided directly distally to the lugs.

21. A device for access to the interior of a body, the device comprising:
   at least one outer part comprising an outer tube;
   an inner tube passing into the outer tube through the outer tube, the inner tube having an inner tube distal tube section with an outer side having radial projections at a distal end of the inner tube distal tube section; and
   an expansion part comprising a proximal section and an expansion section configured to be self-expanding from a compressed configuration to an expanded configuration, wherein the expansion section is in the compressed configuration within a diameter of the outer tube and the expansion section is in the expanded configuration outside the diameter of the outer tube, which is expanded beyond the diameter of the outer tube, with the expansion section extended out of a distal end of the outer tube, the proximal section of the expansion part being connected to the inner tube at the inner tube distal tube section with a positive-locking connection with respect to an axial disconnection direction, wherein the radial projections of the inner tube distal tube section mesh with radially recesses in the proximal section of the expansion part to form the positive-locking connection,
   wherein the outer tube is positive-lockingly connected to a first grip part of a grip, and the inner tube is positive-lockingly connected to a second grip part of the grip; and
   wherein the first grip part of the grip has an inner side with first grip part undercuts having first grip part undercut edges and the outer tube has outwardly directed first part lugs at an outer tube proximal end, the first part lugs being configured to respectively extend behind the first grip part undercut edges, and
   wherein the second grip part of the grip has an inner side with second grip part undercuts having second grip part undercut edges and the inner tube has outwardly directed second part lugs at an inner tube proximal end, the second part lugs being configured to respectively extend behind the second grip part undercut edge.

* * * * *